United States Patent [19]

Clear et al.

[11] Patent Number: 5,575,783
[45] Date of Patent: Nov. 19, 1996

[54] ABSORBENT ARTICLE WITH DYNAMIC ELASTIC FEATURE COMPRISING ELASTICIZED HIP PANELS

[75] Inventors: Sandra H. Clear, Maineville, Ohio; Keith W. Rollag, Ashiya; Hiroshi Nakahata, Hyogo, both of Japan

[73] Assignee: The Procter & Gamble Company, Cincinnati, Ohio

[21] Appl. No.: 225,357

[22] Filed: Apr. 7, 1994

Related U.S. Application Data

[63] Continuation of Ser. No. 951,982, Sep. 28, 1992, abandoned.

[51] Int. Cl.⁶ .................................................. A61F 13/15
[52] U.S. Cl. .................................... 604/385.1; 604/385.2
[58] Field of Search .......................... 604/385.2, 378, 604/385.1; 2/78 B, 78 C, 78.1, 78.2, 78.3, 400–402; 156/163, 164

[56] References Cited

U.S. PATENT DOCUMENTS

| | | | |
|---|---|---|---|
| 854,763 | 5/1907 | Scriven | 2/78 C |
| 2,216,897 | 10/1940 | Zoob | 2/401 |
| 2,344,375 | 3/1944 | Stephens | 2/401 X |
| 3,860,003 | 1/1975 | Buell | 604/385.2 |
| 4,031,568 | 6/1977 | Huff . | |
| 4,351,872 | 9/1982 | Brosseau et al. | 428/198 |
| 4,355,425 | 10/1982 | Jones et al. . | |
| 4,381,781 | 5/1983 | Sciaraffa et al. . | |
| 4,515,595 | 5/1985 | Kievit et al. . | |
| 4,675,016 | 6/1987 | Meuli et al. . | |
| 4,690,681 | 9/1987 | Haunschild et al. . | |
| 4,699,622 | 10/1987 | Toussant et al. . | |
| 4,834,741 | 5/1989 | Sabee | 604/385.2 |
| 4,842,596 | 6/1989 | Kielpikowski et al. | 604/385.2 |
| 4,847,134 | 7/1989 | Fahrenkrug et al. | 156/163 X |
| 4,857,067 | 8/1989 | Wood et al. | 604/389 |
| 4,861,652 | 8/1989 | Lippert et al. . | |
| 4,892,528 | 1/1990 | Suzuki et al. . | |
| 4,892,536 | 1/1990 | Des Marais et al. | 604/385.2 |
| 4,915,767 | 4/1990 | Rajala et al. . | |
| 4,935,021 | 6/1990 | Huffman et al. | 604/385.1 |
| 4,938,753 | 7/1990 | Van Gompel et al. . | |

(List continued on next page.)

FOREIGN PATENT DOCUMENTS

| | | | |
|---|---|---|---|
| 956751 | 10/1974 | Canada | 2/78 C |
| 0323634 | 7/1989 | European Pat. Off. . | |
| 1-58610 | 4/1989 | Japan . | |
| 4028364 | 1/1992 | Japan | 604/385.2 |
| 4-47428 | 4/1992 | Japan . | |
| 2244201 | 11/1991 | United Kingdom . | |

*Primary Examiner*—David H. Willse
*Attorney, Agent, or Firm*—Steven W. Miller; E. Kelly Linman; Jacobus C. Rasser

[57] ABSTRACT

Absorbent articles such as disposable diapers, incontinent briefs, diaper holders, training pants, and the like, that provide dynamic fit about the wearer by the use of elasticized hip panels. Such absorbent articles comprise a liquid pervious topsheet; a liquid impervious backsheet; an absorbent core disposed between the topsheet and the backsheet; elasticized side panels positioned in the side panels of the back waist region; and an elasticized hip panel positioned in the central region of the back waist region. The elasticized hip panel comprises a stretch laminate comprising one or more elongatable components and an elastic hip panel member that are mechanically stretched to allow expansion of the stretch laminate beyond the original planar state of the diaper in the lateral direction. By adding stretch to the middle-back of the absorbent article, the absorbent article is capable of expanding in the back waist region thereby creating a more three-dimensional fit to better contour the hips and buttocks and to more completely wrap the wearer's hips and buttocks. In an alternative embodiment, a single elastic hip panel member is positioned in most of the central region of the back waist region with the stretch laminate being mechanically stretched in selected zones or preferably over the entire area of the elastic hip panel member. The absorbent core is either stretchable or preferably not attached to the stretch laminate in the mechanically stretched zones to not encumber the stretch of the stretch laminate. The topsheet is also preferably stretchable.

16 Claims, 2 Drawing Sheets

U.S. PATENT DOCUMENTS

| | | | |
|---|---|---|---|
| 4,938,757 | 7/1990 | Van Gompel et al. . | |
| 4,940,464 | 7/1990 | Van Gompel et al. . | |
| 5,022,096 | 6/1991 | Pacanowsky | 2/227 |
| 5,055,103 | 10/1991 | Nomura et al. | 604/385.2 |
| 5,080,741 | 1/1992 | Nomura et al. . | |
| 5,092,861 | 3/1992 | Nomura et al. | 604/385.2 |
| 5,143,679 | 9/1992 | Weber et al. . | |
| 5,151,092 | 9/1992 | Buell et al. | 604/385.2 |
| 5,196,000 | 3/1993 | Clear et al. | 604/385.2 |
| 5,366,453 | 11/1994 | Zehner et al. | 604/385.2 |
| 5,449,353 | 9/1995 | Watanabe et al. | 604/385.2 |

5,575,783

ABSORBENT ARTICLE WITH DYNAMIC ELASTIC FEATURE COMPRISING ELASTICIZED HIP PANELS

This is a continuation of application Ser. No. 07/951,982, filed on Sept. 28, 1992, now abandoned.

FIELD OF THE INVENTION

The present invention relates to absorbent articles such as diapers, incontinent briefs, diaper holders, training pants, and the like, and more particularly, to absorbent articles having elastic features providing dynamic fit about the wearer.

BACKGROUND OF THE INVENTION

Infants and other incontinent individuals wear absorbent articles such as diapers to receive and contain urine and other body exudates. Absorbent articles function both to contain the discharged materials and to isolate these materials from the body of the wearer and from the wearer's garments and bed clothing. Disposable absorbent articles having many different basic designs are known to the art. For example, U.S. Pat. Re. No. 26,152, entitled "Disposable Diaper" issued to Duncan and Baker on Jan. 31, 1967, describes a disposable diaper which has achieved wide acceptance and commercial success. In order to provide better fit and reduced leakage about the leg of the wearer, absorbent articles have been provided with elastic leg closures, elastic waist features, and elasticized side panels. U.S. Pat. No. 3,860,003, entitled "Contractable Side Portions For Disposable Diaper", issued to Kenneth B. Buell on Jan. 14, 1975, describes an elasticized leg cuff disposable diaper which has achieved wide acceptance and commercial success.

However, it has been found that absorbent articles having elastic closures still have a tendency to gap away from the wearer during use. These problems have been found to be caused by the relative motions of the wearer during use. As the wearer changes position, there are significant dimensional changes in the waist, stomach, hips, buttocks, and legs. These dimensional changes are particularly noticeable for infants. The circumference of the infant from hip to hip through the buttocks is much bigger than through the front waist/stomach area. Thus, as the wearer moves, conventional diapers are unable to expand and contract in proportion to the circumference of the wearer in the hips through the buttocks due to their construction with relatively non-elastic materials. Thus, the diaper tends to sag, gap and slip to a degree that fit is degraded and the likelihood of leakage is increased. Further, since the diaper cannot expand to accomodate these circumferential changes in dimension, pressure is applied to the body that can cause skin marking.

Thus, it would be advantageous to provide an absorbent article having elastic features that provide better fit.

Therefore, it is an object of the present invention to provide an absorbent article having dynamic fit particularly in the hips through the buttocks.

It is a further object of the present invention to provide an absorbent article having an elastic feature that provides sustained dynamic fit as the wearer moves.

These and other objects of the present invention will be more readily apparent when considered in reference to the following description and when taken in conjunction with the accompanying drawings.

SUMMARY OF THE INVENTION

The present invention provides absorbent articles such as disposable diapers, incontinent briefs, diaper holders, training pants, and the like, that provide dynamic fit around the wearer. Such absorbent articles comprise a liquid pervious topsheet; a liquid impervious backsheet; an absorbent core disposed between the topsheet and the backsheet; an elastic waist feature positioned in the central region of the back waist region; elasticized side panels positioned in the side panels of the back waist region; and an elasticized hip panel positioned in the central region of the back waist region. The elasticized hip panel comprises a stretch laminate comprising one or more elongatable components (typically at least the backsheet) and an elastic hip panel member that are mechanically stretched to allow expansion of the stretch laminate beyond the original planar state of the laminate in the lateral direction. The elasticized hip panel preferably comprises a zero strain stretch laminate. Adding stretch to the middle-back of the absorbent article, in conjunction with the elasticized side panels and the elastic waist feature in the back waist region, creates an absorbent article that is capable of expanding in the back waist region so as to be wider in the back than in the front thereby creating a more three-dimensional fit to better contour to the hips and buttocks. This allows the absorbent article to more completely wrap around the wearer's hips and buttocks and provide stretch which better fits the tops of the legs. As a result, the absorbent article has less gapping at the hips and the sides of the buttocks, helps to prevent leakage in these regions, reduces sagging, and reduces the stress on the diaper in the hip area during use.

In an alternative embodiment of the present invention, a single elastic hip panel member is positioned in most of the central region of the back waist region. The stretch laminate of the elastic hip panel member, the backsheet, and a laminate coversheet is mechanically stretched in selected zones or preferably over the entire area of the elastic hip panel member to provide expansion throughout the central region of the back waist region. The absorbent core is either stretchable or preferably not attached to the stretch laminate in the mechanically stretched zones to not encumber the stretch of the stretch laminate. The topsheet is also preferably stretchable.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings in which like designations are used to designate substantially identical elements, and in which:

DETAILED DESCRIPTION OF THE INVENTION

As used herein, the term "absorbent article" refers to devices which absorb and contain body exudates, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use and, preferably, to be recycled, composted or otherwise disposed of in an environmentally compatible manner). A "unitary" absorbent article refers to absorbent articles which are formed of separate parts united together to form a coordinated entity so that they do not require separate manipulative parts like a separate holder and liner. A preferred embodiment of an absorbent article of the present invention is the unitary disposable absorbent article, diaper 20, shown in FIG. 1. As used herein, the term "diaper" refers to an absorbent article generally worn by infants and incontinent persons that is worn about the lower torso of the wearer. It should be understood, however, that the present invention is also applicable to other absorbent articles such as incontinent briefs, incontinent undergarments, diaper holders and liners, feminine hygiene garments, training pants, and the like.

Figure 1:
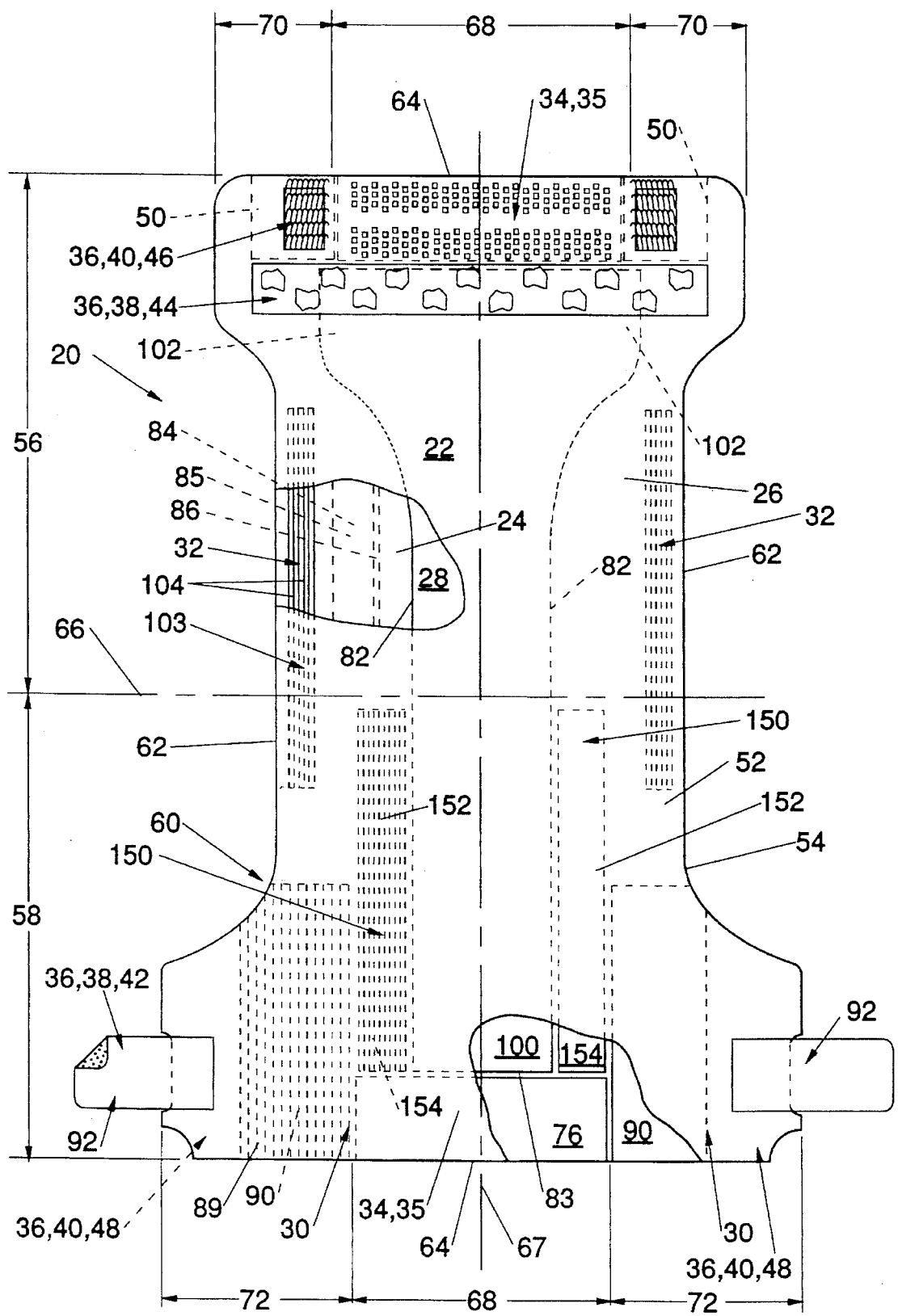
FIG. 1 is a plan view of a disposable diaper embodiment of the present invention having portions cut-away to reveal underlying structure, the outer surface of the diaper facing the viewer.

FIG. 1 is a plan view of the diaper 20 of the present invention in its flat-out, uncontracted state (i.e., with elastic induced contraction pulled out except in the side panels and hip panels wherein the elastic is left in its relaxed condition) with portions of the structure being cut-away to more clearly show the construction of the diaper 20 and with the portion of the diaper 20 which faces away from the wearer, the outer surface 52, facing the viewer. As shown in FIG. 1, the diaper 20 comprises a containment assembly 22 preferably comprising a liquid pervious topsheet 24, a liquid impervious backsheet 26 joined with the topsheet 24, and an absorbent core 28 positioned between the topsheet 24 and the backsheet 26; elasticized side panels 30; elasticized leg cuffs 32; an elastic waist feature 34; a fastening system 36; and elasticized hip panels 150. Each elasticized hip panel 150 comprises a stretch laminate 152 preferably comprising a portion of the backsheet 26, a portion of the topsheet 24, and an elastic hip panel member 154 disposed therebetween.

The diaper 20 is shown in FIG. 1 to have an outer surface 52 (facing the viewer in FIG. 1), an inner surface 54 opposed to the outer surface 52, a front waist region 56, a back waist region 58, and a periphery 60 which is defined by the outer edges of the diaper 20 in which the longitudinal edges are designated 62 and the end edges are designated 64. The inner surface 54 of the diaper 20 comprises that portion of the diaper 20 which is positioned adjacent to the wearer's body during use (i.e., the inner surface 54 generally is formed by at least a portion of the topsheet 24 and other components joined to the topsheet 24). The outer surface 52 comprises that portion of the diaper 20 which is positioned away from the wearer's body (i.e., the outer surface 52 generally is formed by at least a portion of the backsheet 26 and other components joined to the backsheet 26).

The front waist region 56 and the back waist region 58 extend, respectively, from the end edges 64 of the periphery 60 to the lateral centerline 66. The waist regions 56, 58 each comprise a central region 68 and a pair of side panels which typically comprise the outer lateral portions of the waist regions. The side panels positioned in the front waist region 56 are designated 70 while the side panels in the back waist region 58 are designated 72. (In the discussion that follows, unless otherwise noted, the diaper 20 will comprise a pair of side panels in each waist region. While it is not necessary that the pairs of side panels or each side panel be identical, they are preferably mirror images one of the other.) The side panels 72 positioned in the back waist region 58 are elastically extensible in the lateral direction (i.e., elasticized side panels 30). (The lateral direction (x direction or width) is defined as the direction parallel to the lateral centerline 66 of the diaper 20; the longitudinal direction (y direction or length) being defined as the direction parallel to the longitudinal centerline 67; and the axial direction (Z direction or thickness) being defined as the direction extending through the thickness of the diaper 20.)

The containment assembly 22 of the diaper 20 is shown in FIG. 1 as comprising the main body (chassis) of the diaper 20. The containment assembly 22 comprises at least an absorbent core 28 and preferably an outer covering layer comprising the topsheet 24 and the backsheet 26. When the absorbent article comprises a separate holder and a liner, the containment assembly 22 generally comprises the holder and the liner (i.e., the containment assembly 22 comprises one or more layers of material to define the holder while the liner comprises an absorbent composite such as a topsheet, a backsheet, and an absorbent core.) For unitary absorbent articles, the containment assembly 22 comprises the main structure of the diaper with other features added to form the composite diaper structure. Thus, the containment assembly 22 for the diaper 20 generally comprises the topsheet 24, the backsheet 26, and the absorbent core 28.

The absorbent core 28 may be any absorbent means which is generally compressible, conformable, non-irritating to the wearer's skin, and capable of absorbing and retaining liquids such as urine and other certain body exudates. As shown in FIG. 1, the absorbent core 28 has a garment surface 100, a body surface 101, side edges 82, and waist edges 83.

The absorbent core 28 may be manufactured in a wide variety of sizes and shapes (e.g., rectangular, hourglass, "T"-shaped, asymmetric, etc.) and from a wide variety of liquid-absorbent materials commonly used in disposable diapers and other absorbent articles such as comminuted wood pulp which is generally referred to as airfelt. Examples of other suitable absorbent materials include creped cellulose wadding, meltblown polymers including coform, cross-linked cellulosic fibers, tissue including tissue wraps and tissue laminates, absorbent foams, absorbent sponges, superabsorbent polymers, absorbent gelling materials, or any equivalent material or combinations of materials. The configuration and construction of the absorbent core may also be varied (e.g., the absorbent core may have varying caliper zones, a hydrophilic gradient, a superabsorbent gradient, or lower average density and lower average basis weight acquisition zones; or may comprise one or more layers or structures). The total absorbent capacity of the absorbent core 28 should, however, be compatible with the design loading and the intended use of the diaper 20. Further, the size and absorbent capacity of the absorbent core 28 may be varied to accommodate wearers ranging from infants through adults.

A preferred embodiment of the diaper 20 has an asymmetric, modified T-shaped, absorbent core 28 having ears 102 in the front waist region 56 but a generally rectangular shape in the back waist region 58. This configuration allows wider elasticized side panels 30 in the back waist region 58. An exemplary absorbent structure for use as the absorbent core 28 of the present invention that has achieved wide acceptance and commercial success is described in U.S. Pat. No. 4,610,678 entitled "High-Density Absorbent Structures" issued to Weisman and Goldman on Sept. 9, 1986. U.S. Pat. No. 4,673,402 entitled "Absorbent Articles With Dual-Layered Cores" issued to Weisman, Houghton, and Gellert on Jun. 16, 1987; and U.S. Pat. No. 4,888,231 entitled "Absorbent Core Having A Dusting Layer" issued to Angstadt on Dec. 19, 1989; also describe absorbent structures that are useful in the present invention. The absorbent core 28 is preferably the commercially successful absorbent member described in U.S. Pat. No. 4,834,735, entitled "High Density Absorbent Members Having Lower Density and Lower Basis Weight Acquisition Zones", issued to Alemany and Berg on May 30, 1989. The absorbent core may further comprise the dual core system containing an acquisition/distribution core of chemically stiffened fibers positioned over the absorbent storage cores as detailed in co-pending U.S. patent application Ser. No. 07/843,706, "Absorbent Article With Elastic Waist Feature and Enhanced Absorbency", Clear and Alemany, filed on Feb. 28, 1992; and in U.S. Pat. No. 5,147,345, "High Efficiency Absorbent Articles For Incontinence Management", which issued to Young, LaVon and Taylor on Sept. 15, 1992. All of these references are incorporated herein by reference.

The backsheet 26 is positioned adjacent the garment surface 100 of the absorbent core 28 and is preferably joined thereto by attachment means (not shown) such as those well known in the art. For example, the backsheet 26 may be secured to the absorbent core 28 by a uniform continuous layer of adhesive, a patterned layer of adhesive, or an array of separate lines, spirals, or spots of adhesive. Adhesives which have been found to be satisfactory are manufactured by Century Adhesives, Inc. of Columbus, Ohio and marketed as Century 5227; and by H. B. Fuller Company of St. Paul, Minn. and marketed as HL-1258. The attachment means will preferably comprise an open pattern network of filaments of adhesive as is disclosed in U.S. Pat. No. 4,573,986 entitled "Disposable Waste-Containment Garment", which issued to Minetola and Tucker on Mar. 4, 1986, and which is incorporated herein by reference. An exemplary attachment means of an open pattern network of filaments comprises several lines of adhesive filaments swirled into a spiral pattern such as is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Each of these patents are incorporated herein by reference. Alternatively, the attachment means may comprise heat bonds, pressure bonds, ultrasonic bonds, dynamic mechanical bonds, or any other suitable attachment means or combinations of these attachment means as are known in the art.

The backsheet 26 is impervious to liquids (e.g., urine) and is preferably manufactured from a thin plastic film, although other flexible liquid impervious materials may also be used. As used herein, the term "flexible" refers to materials which are compliant and will readily conform to the general shape and contours of the human body. The backsheet 26 prevents the exudates absorbed and contained in the absorbent core 28 from wetting articles which contact the diaper 20 such as bedsheets and undergarments. The backsheet 26 may thus comprise a woven or nonwoven material, polymeric films such as thermoplastic films of polyethylene or polypropylene, or composite materials such as a film-coated nonwoven material. Preferably, the backsheet is a thermoplastic film having a thickness of from about 0.012 mm (0.5 mil) to about 0.051 mm (2.0 mils).

In a preferred embodiment of the present invention, at least a portion of the backsheet 26 is subjected to mechanical stretching in order to provide both a "zero strain" stretch laminate that forms the elasticized side panels 30 and the elasticized hip panels 150 and, optionally, to mechanically prestrain the portion of the backsheet coinciding with the elastic waist feature or the elastic leg feature. Thus, the backsheet 26 is preferably elongatable, most preferably drawable, but not necessarily elastomeric, so that the backsheet 26 will, upon mechanical stretching, be at least to a degree permanently elongated such that it will not fully return to its original undistorted configuration. In preferred embodiments, the backsheet can be subjected to mechanical stretching without undue rupturing or tearing. Thus, it is preferred that the backsheet 26 have an ultimate elongation to break of at least about 400% to about 700% in the cross-machine direction as measured using a method consistent with ASTM D-638. Thus, preferred polymeric films for use as the backsheet contain a high content of linear low density polyethylene. Particularly preferred materials for the backsheet include blends comprised of about 45–90% linear low density polyethylene and about 10–55% polypropylene. Exemplary films for use as the backsheet of the present invention are manufactured by Tredegar Industries, Inc. of Terre Haute, Ind. under the designation RR8220 blend for blown films and RR5475 blend for cast films. The backsheet 26 is preferably embossed (typically, to a caliper of about 0.127 mm (5.5 mils)) and/or matte finished to provide a more clothlike appearance. Further, the backsheet 26 may permit vapors to escape from the absorbent core 28 (i.e., breathable) while still preventing exudates from passing through the backsheet 26.

The size of the backsheet 26 is dictated by the size of the absorbent core 28 and the exact diaper design selected. In a preferred embodiment, the backsheet 26 has a modified hourglass shape extending beyond the absorbent core 28 around the entire diaper periphery 60. Preferably, the backsheet 26 is much wider than the absorbent core 28 in the back waist region 58 so that the side panels 72 and the portion of the central region 68 wherein the absorbent core is not disposed, the hip panels 69, are generally wide.

The topsheet 24 is positioned adjacent the body surface 101 of the absorbent core 28 and is preferably joined thereto and to the backsheet 26 by attachment means (not shown) such as those well known in the art. Suitable attachment means are described with respect to joining the backsheet 26 to the absorbent core 28. As used herein, the term "joined" encompasses configurations whereby an element is directly secured to the other element by affixing the element directly to the other element, and configurations whereby the element is indirectly secured to the other element by affixing the element to intermediate member(s) which in turn are affixed to the other element. In a preferred embodiment of the present invention, the topsheet 24 and the backsheet 26 are joined directly to each other in the diaper periphery 60 and are indirectly joined together by directly joining them to the absorbent core 28 by the attachment means (not shown).

The topsheet 24 is compliant, soft feeling, and non-irritating to the wearer's skin. Further, the topsheet 24 is liquid pervious permitting liquids (e.g., urine) to readily penetrate through its thickness. A suitable topsheet may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. Preferably, the topsheet 24 is made of a hydrophobic material to isolate the wearer's skin from liquids contained in the absorbent core 28 (i.e., prevent "rewet").

In a preferred embodiment of the present invention, at least a portion of the topsheet 24 is subjected to mechanical stretching in order to provide a "zero strain" stretch laminate that forms the elasticized side panels 30 and the elasticized hip panels 150. Thus, the topsheet 24 is preferably elongatable, most preferably drawable, but not necessarily elastomeric, so that the topsheet 24 will, upon mechanical stretching, be at least to a degree permanently elongated such that it will not fully return to its original configuration. In preferred embodiments, the topsheet 24 can be subjected to mechanical stretching without undue rupturing or tearing of the topsheet. Thus, it is preferred that the topsheet 24 have a low cross-machine direction (lateral direction) yield strength.

There are a number of manufacturing techniques which may be used to manufacture the topsheet 24. For example, the topsheet 24 may be a nonwoven web of fibers. When the topsheet comprises a nonwoven web, the web may be spunbonded, carded, wet-laid, meltblown, hydroentangled, combinations of the above, or the like. A preferred topsheet is carded and thermally bonded by means well known to those skilled in the fabrics art. A preferred topsheet comprises staple length polypropylene fibers having a denier of about 2.2. As used herein, the term "staple length fibers" refers to those fibers having a length of at least about 15.9 mm (0.625 inches). Preferably, the topsheet has a basis weight from about 18 to about 25 grams per square meter. A suitable topsheet is manufactured by Veratec, Inc., a Division of International Paper Company, of Walpole, Mass. under the designation P-8.

The diaper 20 preferably comprises an elastic leg feature 32 for providing improved containment of liquids and other body exudates. Each elastic leg feature 32 may comprise several different embodiments for reducing the leakage of body exudates in the leg region. (The leg feature can be and is sometimes also referred to as leg bands, side flaps, barrier cuffs, or elastic cuffs.) U.S. Pat. No. 3,860,003 describes a disposable diaper which provides a contractible leg opening have a side flap and one or more elastic members to provide an elasticized leg cuff (gasketing cuff). U.S. Pat. No. 4,909,803 entitled "Disposable Absorbent Article Having Elasticized Flaps" issued to Aziz, et al. on Mar. 20, 1990, describes a disposable diaper having "stand-up" elasticized flaps (barrier cuffs) to improve the containment of the leg regions. U.S. Pat. No. 4,695,278 entitled "Absorbent Article Having Dual Cuffs" issued to Lawson on Sept. 22, 1987, describes a disposable diaper having dual cuffs including a gasketing cuff and a barrier cuff. While each elastic leg feature 32 may be configured so as to be similar to any of the leg bands, side flaps, barrier cuffs, or elastic cuffs described above, it is preferred that each elastic leg feature 32 comprise an elasticized gasketing cuff 103 and a barrier leg cuff 84 such as described in the above referenced U.S. Pat. No. 4,695,278. As shown in FIG. 1, the elasticized gasketing cuff 103 comprises a portion of the topsheet 24, a portion of the backsheet 26, and a plurality of elastic members 104 positioned therebetween while the elasticized barrier cuff 84 comprises a barrier flap 85 and one or more spacing elastic members 86.

The diaper 20 preferably further comprises an elastic waist feature 34 that provides improved fit and containment. The elastic waist feature 34 is that portion or zone of the diaper 20 which is intended to elastically expand and contract to dynamically fit the wearer's waist. The elastic waist feature 34 at least extends longitudinally outwardly from at least one of the waist edges 83 of the absorbent core 28 and generally forms at least a portion of the end edge 64 of the diaper 20. Disposable diapers are generally constructed so as to have two elastic waist features, one positioned in the front waist region and one positioned in the back waist region, although diapers can be constructed with a single elastic waist feature. Further, while the elastic waist feature or any of its constituent elements can comprise a separate element affixed to the diaper, the elastic waist feature 34 is preferably constructed as an extension of other elements of the diaper 20 such as the backsheet 26 or the topsheet 24, preferably both the backsheet 26 and topsheet 24. As shown in FIG. 1, the elastic waist feature 34 comprises an elasticized waistband 35 which at least comprises an elastic waist member 76, preferably comprising a crosslinked natural rubber foam, operatively associated between the topsheet 24 and the backsheet 26. The elasticized waistband 35 may be constructed in a number of different configurations including that described in U.S. Pat. No. 4,515,595 issued to Kievit, et al. on May 7, 1985. In a particularly preferred embodiment, the elastic waist feature comprises those described in U.S. patent application Ser. No. 07/750,775 of Buell, Clear and Falcone, filed on Aug. 22, 1991, allowed. Each of these references are incorporated herein by reference.

The diaper 20 further comprises elasticized side panels 30 disposed in the back waist region 58. (As used herein, the term "disposed" is used to mean that an element(s) of the diaper is formed (joined and positioned) in a particular place or position as a unitary structure with other elements of the diaper or a separate element joined to another element of the diaper. The elasticized side panels 30 provide an elastically extensible, preferably elastically expandable, feature that provides a more comfortable and contouring fit by initially conformably fitting the diaper to the wearer and sustaining this fit throughout the time of wear well past when the diaper has been loaded with exudates since the elasticized side panels allow the side of the diaper to expand and contract. The elasticized side panels 30 further provide more effective application of the diaper 20 since even if the diaperer pulls one elasticized side panel farther than the other during application (asymmetrically), the diaper 20 will "self-adjust" during wear. While the diaper 20 of the present invention has the elasticized side panels 30 disposed in the back waist region 58; alternatively, the diaper 20 may also be provided with elasticized side panels 30 disposed in the front waist region 56. While the elasticized side panels 30 may be constructed in a number of configurations, examples of diapers with elasticized side panels positioned in the ears (ear flaps) of the diaper are disclosed in U.S. Pat. No. 4,857,067 entitled "Disposable Diaper Having Shirred Ears" issued to Wood, et al. on Aug. 15, 1989; U.S. Pat. No. 4,381,781 issued to Sciaraffa, et al. on May 3, 1983; U.S. Pat. No. 4,938,753 issued to Van Gompel, et al. on Jul. 3, 1990; and the hereinbefore referenced U.S. patent application Ser. No. 07/750,775 of Buell, Clear and Falcone, filed on Aug. 22, 1991, allowed; each of which are incorporated herein by reference. The preferred elasticized side panels 30 comprise a side panel stretch laminate 89 comprising an elongatable component(s) (typically a portion of the topsheet 24 and a portion of the backsheet 26) and an elastic side panel member 90 positioned therebetween that is mechanically stretched. The side panel stretch laminate 89 preferably comprises a zero strain stretch laminate formed using the method and apparatus as described herein with respect to the elasticized hip panels and in U.S. Pat. No. 5,143,679.

Figure 2:
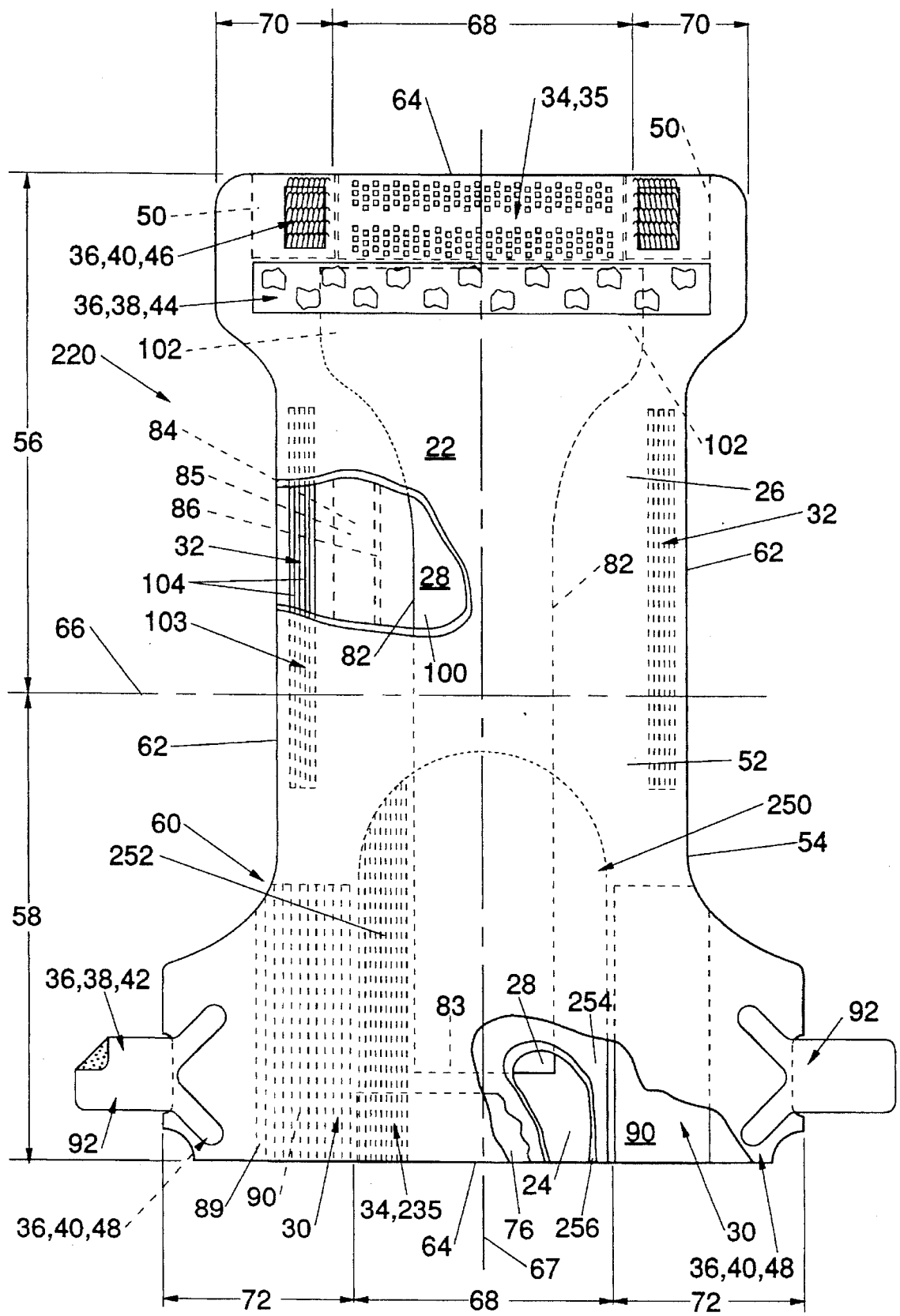
FIG. 2 is a plan view of an alternative disposable diaper embodiment of the present invention having portions cut-away to reveal underlying structure, the outer surface of the diaper facing the viewer.

The diaper 20 is also provided with a fastening system 36 which forms a side closure which maintains the front waist region 56 and the back waist region 58 in an overlapping configuration such that lateral tensions are maintained around the circumference of the diaper to maintain the diaper on the wearer. Exemplary fastening systems are disclosed in U.S. Pat. No. 4,846,815 entitled "Disposable Diaper Having An Improved Fastening Device" issued to Scripps on Jul. 11, 1989; U.S. Pat. No. 4,894,060 entitled "Disposable Diaper With Improved Hook Fastener Portion" issued to Nestegard on Jan. 16, 1990; U.S. Pat. No. 4,946,527 entitled "Pressure-Sensitive Adhesive Fastener and Method of Making Same" issued to Battrell on Aug. 7, 1990; U.S. Pat. No. 3,848,594 entitled "Tape Fastening System for Disposable Diaper" issued to Buell on Nov. 19, 1974; and U.S. Pat. No. B14,662,875 entitled "Absorbent Article" issued to Hirotsu, et al. on May 5, 1987. In a preferred embodiment, the diaper is provided with a closure system (tensioning means) for dynamically creating/maintaining lateral tension through the elasticized waistband 35. The lateral tension dynamically created and maintained by the closure system "activates" the stretch of the elasticized waistband 35 thereby allowing it to more dynamically expand and contract with the motions of the wearer. Gapping of the elasticized waistband is also reduced by the activated stretch since it is held in tension to snugly fit against the wearer's waist both when the diaper is initially fitted to the wearer and during use. While the closure system may take on a number of configurations such as adhesive tape tabs, mechanical closure tape tabs, fixed position fasteners, or any other means for tensioning the elasticized waistband 35 as are known in the art, as shown in FIG. 1, the closure system preferably comprises a waist closure system 40 comprising at least one, typically a pair of, first attachment components 46 and at least one second attachment component 48. More preferably, the fastening system 36 additionally comprises a primary fastening system 38 such that the diaper 20 has a dual tension fastening system. Preferred embodiments of a diaper having a dual tension fastening system are described in commonly assigned, co-pending, U.S. patent application Ser. No. 07/714,476, P&G Case 4412, Weil, et al., "Absorbent Article With Fastening System Providing Dynamic Elasticized Waistband Fit", filed Jun. 13, 1991; and the above referenced U.S. patent application Ser. No. 07/750,775 of Buell, et al. filed on Aug. 22, 1991, allowed; the specifications and drawings of each being incorporated herein by reference. (In an alternative embodiment as shown in FIG. 2, the tape tabs 92 have a Y-shaped closure on the backsheet side to provide improved distribution of stretch in the elasticized side panels 30.)

The diaper 20 additionally preferably comprises a positioning patch 50 located subjacent the first attachment component 46. The positioning patch 50 raises the first attachment component 46 in the Z-direction (thickness) to allow the first attachment component 46 to come in better contact with the second attachment component 48 and allow the waist closure system 40 to more easily be closed (with less effort). Thus, the waist closure system 40 is more effectively passively activated. The positioning patch 50 also provides a zone of increased flexural stiffness that reduces the tendency of the flexible ear flaps to fold over onto the first attachment component(s) 46 thereby occluding the hooks from being secured during diaper application. Thus, the positioning patch 50 can comprise any element that provides a Z-direction build-up to the first attachment components 46. As shown in FIG. 1, the positioning patches 50 each comprise a rectangular-shaped piece of material positioned subjacent the first attachment component 46. While the positioning patches 50 may be positioned directly subjacent the first attachment components 46, the positioning patches 50 are preferably positioned between the topsheet 24 and the backsheet 26. In order to provide a flexurally stiff circumference about the waist of the wearer, the lateral edges of the positioning patches can be abutted to or slightly overlapped with the side edges of the elastic waistband member 76.

The diaper 20 comprises one or more elasticized hip panels 150 disposed in the central region 68 of the back waist region 58. Each elasticized hip panel 150 provides an elastically expandable feature that provides a more comfortable and contouring fit about the hips and buttocks of the wearer by initially conformably fitting the diaper 20 to the hips/buttocks and sustaining this fit throughout the time of wear since the elasticized hip panels 150 allow portions of the central region 68 of the back waist region 58 of the diaper 20 to elastically expand with the body and return to the original configuration as the body moves. This additional stretch in the middle-back of the diaper allow the diaper to better wrap around the wearer's hips and buttocks. As a result, the diaper fits better to the body and reduces sagging, gapping, and back waistband slippage. The elasticized hip panels 150 thus can improve the fit of the diaper and help to prevent leakage.

The diaper may have one or a plurality of elasticized hip panels disposed in the central region 68 of the back waist region 58. In one embodiment as discussed hereinafter, the diaper may have only one elasticized hip panel providing stretch throughout a large area of the back waist region 58. In another embodiment as shown in FIG. 1, the diaper 20 has a pair of elasticized thigh panels 150, one positioned laterally outwardly from each side edge 82 of the absorbent core 28. In this embodiment, each elasticized thigh panel 150 is disposed in a discrete zone in the back waist region 58 defined as the area disposed laterally outwardly from the side edge 82 of the absorbent core, laterally inwardly from the elasticized side panel 30, and longitudinally inwardly from the elastic waist feature 34. Thus, in this embodiment, the elasticized hip panel 150 is bounded by the absorbent core 28, the elasticized side panels 30, the elastic waist feature 34, and the lateral centerline 66.

The elasticized hip panels 150 are elastically expandable in at least one direction, preferably the lateral direction, to provide better fit by providing elastic expansion that follows the hips/buttocks. It should be noted, however, that the elasticized hip panels 150 may be elastically expandable in any other direction or in more than one direction. As discussed hereinafter, lateral expansion is preferred and achieved by stretching the stretch laminate 152 of the elasticized hip panels 150 generally perpendicular to the lateral direction.

Each elasticized hip panel 150 comprises a stretch laminate 152 so that the elasticized hip panels are capable of expanding beyond the original planar state of the diaper 20. The stretch laminate 152 comprises an elastic hip panel member 154 and one or more elongatable components (e.g., the backsheet 26 and another elongatable component layer which in the embodiment shown in FIG. 1 is the topsheet 24) that have been mechanically stretched as hereinafter described. This stretch laminate 152 allows for expansion of the elasticized hip panel 150 beyond the initial dimension of the elongatable components to follow the dimensions of the hips/buttocks during movement.

While the stretch laminate 152 may be constructed in a number of configurations; in a preferred embodiment as shown in FIG. 1, the stretch laminate 152 comprises a portion of the topsheet 24, a portion of the backsheet 26, and an elastic hip panel member 154 operatively associated with the topsheet 24, the backsheet 26 or both, most preferably between the topsheet 24 and the backsheet 26. In an especially preferred embodiment of the present invention, the elastic hip panel members 154 are operatively associated in an untensioned state so as to form "zero strain" stretch laminates. As used herein, the term "zero strain" stretch laminate refers to a laminate comprised of at least two plies of material which are secured to one another along at least a portion of their coextensive surfaces while in a substantially untensioned ("zero strain") condition; one of the plies comprising a material which is stretchable and elastomeric (i.e., it will return substantially to its untensioned dimensions after an applied tensile force has been released) and a second ply which is elongatable (but not necessarily elastomeric) so that upon stretching the second ply will be, at least to a degree, permanently elongated so that upon release of the applied tensile forces it will not fully return to its original undeformed configuration. The resulting "zero strain" stretch laminate is thereby rendered elastically expandable, at least up to the point of initial stretching, in the direction of initial stretching by mechanically stretching the laminate. Examples of such "zero strain" stretch laminates are disclosed in U.S. Pat. No. 2,075,189 issued to Galligan, et al. on Mar. 30, 1937; U.S. Pat. No. 3,025,199 issued to Harwood on Mar. 13, 1962; U.S. Pat. No. 4,107,364 issued to Sisson on Aug. 15, 1978; U.S. Pat. No. 4,209,563 issued to Sisson on Jun. 24, 1980; and U.S. Pat. No. 4,834,741 issued to Sabee on May 30, 1989. Each of these patents are incorporated herein by reference. Alternatively, the elastic hip panel member 154 can be operatively associated in a tensioned condition and the resulting laminate then subjected to mechanical stretching to form a pretensioned stretch laminate. For example, the elastic hip panel member may be operatively associated with the elongatable component in an elastically contractible condition so that the elastic hip panel member gathers or contracts the stretch laminate. While either of the elasticized hip panels 150 may comprise a pretensioned stretch laminate or a zero strain stretch laminate, in a preferred embodiment, both elasticized hip panels 150 comprise the same type of stretch laminate, most preferably each comprises a zero strain stretch laminate.

At least a portion of the stretch laminate 152 containing the elastic hip panel member 154 is subjected to mechanical stretching sufficient to permanently elongate the elongatable components (e.g., the backsheet 26 and the topsheet 24) of the stretch laminate 152. The stretch laminate 152 is then allowed to return to its substantially untensioned condition. Particularly preferred methods and apparatus used for making stretch laminates out of an elongatable component(s) (the topsheet and the backsheet) and an elastomeric member positioned between the same, use meshing corrugated rolls to mechanically stretch the components. A discussion of suitable apparatus and methods for mechanically stretching portions of a diaper is contained in U.S. Pat. No. 4,107,364 issued to Sisson on Aug. 15, 1978 and U.S. Pat. No. 4,834,741 issued to Sabee on May 30, 1989. Particularly preferred apparatus and methods are disclosed in U.S. Pat. No. 5,143,679, "Method for Sequentially Stretching Zero Strain Stretch Laminate Web to Impart Elasticity Thereto Without Rupturing the Web" issued to Weber and Richardson on Sept. 1, 1992; and in co-pending, commonly assigned, U.S. patent application Ser. No. 07/662,536 entitled "Improved Method and Apparatus for Incrementally Stretching a Zero Strain Stretch Laminate to Impart Elasticity Thereto"; P&G Case 4339; filed by Gerald M. Weber, et al. on Feb. 28, 1991, allowed; and U.S. patent application Ser. No. 07/662,537 entitled "Improved Method and Apparatus for Incrementally Stretching Zero Strain Stretch Laminate Web in a Non-Uniform Manner to Impart a Varying Degree of Elasticity Thereto"; P&G Case 4340; filed by Kenneth B. Buell, et al. on Feb. 28, 1991, allowed; each of the above references being incorporated herein by reference. In the preferred method for forming the elasticized hip panels 150 constructed using the "zero strain" stretch laminate technology herein disclosed, the meshing teeth on the pairs of corrugated rolls employed to incrementally mechanically stretch the "zero strain" stretch laminate of the elasticized hip panel 150 are arranged in a desired configuration, preferably perpendicular to the lateral direction to produce expansion in the lateral direction as depicted by the dashed lines in a portion of FIG. 1.

The elastic hip panel member 154 may take on a number of different sizes, shapes, configurations and materials. One elastomeric material which has been found to be especially suitable for use as the elastic hip panel member 154 (especially for "zero strain" stretch laminates) is an elastomeric foam having an elongation to break of at least about 400% and an extension force of about 200 grams/in of sample width at 50% extension of its unstrained length. Exemplary elastomeric foams which have been found suitable for use as the elastic hip panel member 154 include: (a) crosslinked natural rubber foams preferably having a caliper of approximately 50 mils and a density of 13.3 lbs/cu ft. (0.214 g/cm$^3$), such as available from Fulflex, Inc. of Middletown, R.I.; or as available from Ludlow Composites Corporation of Freemont, Ohio and marketed under the tradename Babyfoam; or polyurethane foams having a caliper of approximately 80 mils and a density of approximately 2.06 lbs/cu ft. (0.033 g/cm$^3$) such as available from Bridgestone of Yokahama, Japan and marketed under the tradename Bridgestone SG polyurethane foam; or as available from General Foam of Paramis, N.J. and marketed under the designation of polyurethane foam No. 40310. Another exemplary elastomeric material is elastomeric adhesives such as the pressure-sensitive elastomeric adhesive marketed by the Findley Adhesives Corporation of Wauwatosa, Wis. under the tradename 198-338. Other suitable elastomeric materials for use as the elastic hip panel members 154 include "live" synthetic or natural rubber, other synthetic or natural rubber foams, elastomeric films (including heat shrinkable elastomeric films), elastomeric scrim, elastomeric woven or nonwoven webs, elastomeric composites such as elastomeric nonwoven laminates, or the like. As shown in FIG. 1, the elastic hip panel members 154 each preferably comprise a patch of elastomeric material (elastomeric patch). The length and width of the elastomeric hip panel members 154 are dictated by the diaper's functional design. In the particular embodiment shown in FIG. 1, the elastic hip panel members 154 have a rectangular shape extending from the inward edge of the elasticized waistband 35 toward the longitudinal centerline 66 between the side edges 82 of the absorbent core 28 and the elasticized side panels 30. However, many other shapes are possible in the design of the elastic hip panel members 154.

The diaper 20 is preferably applied to a wearer by positioning the back waist region 58 under the wearer's back and drawing the remainder of the diaper between the wearer's legs so that the front waist region 56 is positioned across the front of the wearer. The tab portions of the tape tabs 92 are then released. The diaper then wraps the elasticized side panel 30 around the wearer, while still grasping the tab. The elasticized side panels 30 and the elasticized hip panels 150 will typically be extended in tension during this operation so as to conform to the size and shape of the wearer. The fastening component is secured to the second fastening component to affect the side closure for the diaper.

FIG. 2 shows an alternative embodiment of the present invention wherein a single elastic hip panel member 254 is positioned in the central region 68 of the back waist region 58. As shown in FIG. 2, the elastic hip panel member 254 has an elongated semi-elliptical shape so that almost the entire central region 68 of the back waist region 58 is rendered elastically expandable. In this embodiment, the elastic hip panel member 254 comprises an elastomeric adhesive such as hereinbefore described. The stretch laminate 252 preferably comprises a portion of the backsheet 26, a laminate coversheet 256, and the elastic hip panel member 254 disposed therebetween. A laminate coversheet 256 is provided between the elastic hip panel member 254 and the absorbent core 28 so that the stretch laminate 252 may be activated by mechanical stretching prior to positioning the absorbent core 28 on the stretch laminate 252. The stretch laminate 252 is preferably activated by mechanical stretching over its entire area; although, as discussed hereinafter, the stretch laminate may be activated in only selective zones. The stretch laminate 252 is preferably activated to provide stretch in at least the lateral direction as indicated by the dashed lines in part of FIG. 2. (The apparatus used to stretch this laminate can have teeth having a width of 0.030 inches, a pitch of 0.150 inches, a depth of 0.290 inches, and an activation force of 110 g/in.). Since the stretch laminate 252 is over the entire center back of the diaper, the absorbent core is preferably allowed to "float" (be unattached to the stretch laminate 252) in selected zones or over the entire area so that the stretch laminate 252 is allowed to freely stretch without being encumbered by the absorbent core 28. In this particular embodiment, the absorbent core 28 is unattached to the stretch laminate over its entire extent. Further, the topsheet 24 is stretchable so as to not inhibit the stretch of the stretch laminate 252. As shown in FIG. 2, the elastic hip panel member 254 extends into the elasticized waistband 235. While the elasticized waistband 235 could be formed as a portion of the stretch laminate 252, it preferably additionally comprises an elastic waist member 76 preferably comprising a crosslinked natural rubber foam. The elasticized side panels 30 are constructed in a way to be similar to those shown in FIG. 1. The tape tabs 92 preferably have a Y-shaped closure to provide improved distribution of stretch in the elasticized side panels 30. With this "floating core" overall elasticized hip panel embodiment, the diaper is allowed to more completely wrap around the hips and buttocks of the wearer and provide elastic expansion to thereby better fit the wearer.

As previously discussed, the single elastic hip panel member 254 can be mechanically stretched, "activated", in selected zones or over in its entire area in the central region 68 to provide one or more elasticized hip panels 250. For example, the stretch laminate 252 comprising the elastic hip panel member 254 can be mechanically stretched in two rectangular zones, one laterally outwardly from each side edge 82 of the absorbent core 28. When the elastic hip panel member 254 is selectively activated in the central region laterally outwardly from the side edges of the absorbent core, the diaper acts in a similar way as the diaper embodiment depicted in FIG. 1 except that the elastic hip panel member comprises one piece of elastomeric material. Thus, the stretch laminate 252 can be mechanically stretched in many different zones to provide expansion in desired directions. In the embodiment shown in FIG. 2, the stretch laminate 252 is mechanically stretched over the entire area of the elastic hip panel member 254. Further, in the embodiment shown in FIG. 2, the stretch laminate 252 comprises a portion of the backsheet 26; a laminate coversheet 256, preferably comprising a nonwoven material similar to those suitable for use as the topsheet, more preferably carded polyproplylene fiber nonwoven such as the P-8 material described herein; and an elastic hip panel member 254 preferably comprising an elastomeric adhesive such as that described herein.

When the elastic hip panel member 254 is activated over its entire area, it is preferable to allow the portion of the stretch laminate 252 positioned axially below the absorbent core 28 to stretch to allow even better fit about the hips/buttocks of the wearer. This presents an issue in that the absorbent core 28 is typically not stretchable and would inhibit the stretch of the stretch laminate 252 in the zones where the absorbent core contacts the stretch laminate if it was conventionally joined to the stretch laminate. This is solved by either making the absorbent core stretchable or not attaching the absorbent core to the stretch laminate entirely or in discrete zones. In this latter approach, the absorbent core is allowed to "float" over the stretch laminate area by not securing portions or all of the absorbent core to the stretch laminate. For example, only the ends of the absorbent core are secured to the stretch laminate or specific zones are not attached by using a pattern of bonds such as spots, spirals, or stripes which provide intermittent bonding. In the first approach, the absorbent core can be made stretchable in a number of ways. For example, the absorbent core 28 can be mechanically stretched along with the stretch laminate 252 using the process as hereinbefore described. Thus, the absorbent core 28, an elongatable component of the stretch laminate 252, becomes stretchable by the mechanical stretching process. In this execution, the stretchable absorbent core preferably comprises a web of fibers comprising polypropylene fibers and superabsorbent fibers such as is described in U.S. patent application Ser. No. 07/915,133, "Stretchable Absorbent Articles" filed by Thomas W. Osborn, et al. on Jul. 23, 1992, the specification of which is incorporated herein by reference. The apparatus for stretching the overall laminate would preferably have a rib width of 0.030 inches, a pitch of 0.150 inches and a depth of 0.150 inches with an activation force of 33.3 g/in. Alternatively, the absorbent core itself can be made stretchable or elastically extensible such as is described in the Osborn application incorporated herein by reference.

In addition, it is preferred that the topsheet 24 of the diaper 220 also be stretchable. The topsheet 24 can be made stretchable by either using a stretchable topsheet material or activating selected portions or all of the topsheet by either passing the topsheet through the mechanical stretching apparatus prior to bonding the topsheet onto the diaper (mechanically prestraining the topsheet), or by mechanically stretching the topsheet in conjunction with the stretch laminate 252. Preferred topsheets having stretchability are disclosed in U.S. patent application Ser. No. 07/915,133, "Stretchable Absorbent Articles" filed by Thomas W. Osborn, et al. on Jul. 23, 1992, and U.S. Pat. No. 5,037,416, "Disposable Absorbent Article Having Elastically Extensible Topsheet", which issued to Allen and Freeland on Aug. 6, 1991. Each of these references are incorporated herein by reference.

In a further alternative embodiment of the present invention, improved fit can also be achieved by an elongatable hip panel. In this embodiment, the hip panel can stretch but is not elastic. This nonelastic stretch is achieved by eliminating the elastic hip panel member from the laminate. Thus, only elongatable components are mechanically stretched to permanently elongate/deform the materials in this zone.

In another alternative embodiment, the elastic waist member 76 and/or the elastic side panel member 90 and the elastic hip panel member 154 or 254 can be formed from a single piece or layer of elastomeric material. Thus, the elasticized hip panel 150 or 250 and the elasticized side panel 30 and/or the elasticized waistband 35 can be formed from the same piece of material.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable absorbent article having a first waist region, a second waist region having a central region and a side panel on each side of said central region, a longitudinal centerline, a lateral centerline, longitudinal edges, and end edges, the absorbent article having comprising:

a liquid pervious topsheet;

a liquid impervious backsheet joined to said topsheet;

an absorbent core having side edges and waist edges and being disposed between said topsheet and said backsheet;

an elasticized side panel disposed in each said side panel of said second waist region, each said elasticized side panel being elastically extensible in the lateral direction; and an elasticized hip panel disposed in said central region of said second waist region at least longitudinally inwardly from said waist edge of said absorbent core toward said lateral centerline, said elasticized hip panel comprising a stretch laminate comprising a portion of said backsheet and an elastic hip panel member, at least a portion of said elastic hip panel member extending longitudinally outwardly from each said side edge of said absorbent core, said stretch laminate being mechanically stretched so that said backsheet is, at least to a degree, permanently elongated so as to not fully return to its original undeformed configuration such that said elasticized hip panel member is capable of elastically expanding beyond the original planar state of the absorbent article in at least the lateral direction to fit about the hips and buttocks.

2. The absorbent article of claim 1 wherein said stretch laminate is activated by mechanically stretching in the zones wherein said elastic hip panel member extends laterally outwardly from each side edge of said absorbent core.

3. The absorbent article of claim 1 wherein said stretch laminate is activated by mechanically stretching over the entire area of said elastic hip panel member.

4. The absorbent article of claim 3 wherein said absorbent core is stretchable to allow unencumbered expansion of said stretch laminate.

5. The absorbent article of claim 3 wherein said stretch laminate additionally comprises a portion of said absorbent core.

6. The absorbent article of claim 5 wherein said stretch laminate additionally comprises a portion of said topsheet.

7. The absorbent article of claim 5 wherein said elastic hip panel member comprises an elastomeric foam.

8. A disposable absorbent article having a first waist region, second waist region having a central region and a side panel on each side of said central region, longitudinal edges, and end edges, the absorbent article comprising:

a liquid pervious topsheet;

a liquid impervious backsheet joined to said topsheet;

an absorbent core having side edges and disposed between said topsheet and said backsheet;

an elasticized side panel disposed in each said side panel of said back waist region, each elasticized side panel being elastically extensible in the lateral direction;

an elasticized hip panel disposed in said central region of said second waist region, said hip elasticized hip panel comprising a stretch laminate comprising a portion of said backsheet, a laminate coversheet positioned between said backsheet and said absorbent core, and an elastic hip panel member disposed between said backsheet and said laminate coversheet, said elastic hip panel member extending longitudinally inwardly from said end edge of the absorbent article to about said longitudinal centerline and extending laterally outwardly from each said side edge of said absorbent core to about said elasticized side panel, said stretch laminate being mechanically stretched over the entire area of said elastic hip panel so that said backsheet and said laminate coversheet are, at least to a degree, permanently elongated so as to not fully return to their original undeformed configuration such that said elasticized hip panel is capable of elastically expanding beyond the original planar state of the absorbent article on at least the lateral direction; and said absorbent core being unsecured to said stretch laminate in at least selected zones to allow unencumbered expansion of said stretch laminate.

9. The absorbent article of claim 8 wherein said topsheet is stretchable in at least said central region.

10. The absorbent article of claim 9 wherein said stretch laminate comprises a zero strain stretch laminate.

11. The absorbent article of claim 10 wherein said elastic hip panel member comprises an elastomeric adhesive.

12. The absorbent article of claim 11 wherein each said elastic panel member has a semi-elliptical shape.

13. The absorbent article of claim 12 wherein said absorbent core is unsecured to said stretch laminate over the entire area of said stretch laminate.

14. A disposable absorbent article having a first waist region, a second waist region having a central region and a side panel on each side of said central region, longitudinal edges, and end edges, the absorbent article comprising:

a liquid pervious topsheet;

a liquid impervious backsheet joined to said topsheet;

an absorbent core having side edges and waist edges, said absorbent core being disposed between said topsheet and said backsheet;

an elastic waist feature extending longitudinally outwardly from said waist edge of said absorbent core in said central region of said second waist region;

an elasticized side panel disposed in each said side panel of said second waist region, each said elasticized side panel being elastically extensible in the lateral direction; and an elasticized hip panel disposed in said central region of said second waist region laterally outwardly from each said side edge of said absorbent core, laterally inwardly of said elasticized side panel, and longitudinally inwardly from said elastic waist feature, each said elasticized hip panel comprising a stretch laminate comprising a portion of said backsheet, a portion of said topsheet, and an elastic hip panel member positioned between said topsheet and said backsheet, each said stretch laminate being mechanically stretched so that said backsheet and said topsheet are, at least to a degree, permanently elongated so as to not fully return to their original undeformed configuration such that each said elasticized hip panel is capable of elastically expanding beyond the original planar state of the absorbent article in at least the lateral direction.

15. The absorbent article of claim 14 wherein each said elasticized hip panel comprises a zero strain stretch laminate.

16. The absorbent article of claim 15 wherein each said elasticized side panel comprises a stretch laminate, said stretch laminate comprising a portion of said topsheet, a portion of said backsheet, and an elastic side panel member positioned therebetween, said stretch laminate being mechanically stretched.

* * * * *

UNITED STATES PATENT AND TRADEMARK OFFICE
CERTIFICATE OF CORRECTION

PATENT NO. : 5,575,783
DATED : November 19, 1996
INVENTOR(S) : Sandra H. Clear, et. al.

It is certified that error appears in the above-indentified patent and that said Letters Patent is hereby corrected as shown below:

Column 15, line 18, delete "having".
Column 15, line 35, "longitudinally" should read -- laterally --.
Column 16, line 4, "back" should read -- second --.
Column 16, line 15, "longitudinal" should read -- lateral --.
Column 16, line 19, after "panel" insert -- member --.
Column 16, line 25, "on" should read -- in --.

Signed and Sealed this

Twenty-ninth Day of July, 1997

*Attest:*

BRUCE LEHMAN

*Attesting Officer*  Commissioner of Patents and Trademarks